United States Patent
Berthiaume et al.

(10) Patent No.: US 9,283,382 B2
(45) Date of Patent: Mar. 15, 2016

(54) INTERVENTIONAL MEDICAL SYSTEMS, TOOLS, AND ASSOCIATED METHODS

(71) Applicant: Medtronic, Inc., Minneapolis, MN (US)

(72) Inventors: William A. Berthiaume, Santa Rosa, CA (US); Don H. Tran, Novato, CA (US); Brent L. Locsin, San Francisco, CA (US); Maria E. Valdovinos, Santa Rosa, CA (US); H. Allan Steingisser, Santa Rosa, CA (US); Erik Griswold, Penngrove, CA (US)

(73) Assignee: Medtronic, Inc., Minneapolis, MN (US)

( * ) Notice: Subject to any disclaimer, the term of this patent is extended or adjusted under 35 U.S.C. 154(b) by 91 days.

(21) Appl. No.: 14/242,123

(22) Filed: Apr. 1, 2014

(65) Prior Publication Data
US 2015/0273212 A1  Oct. 1, 2015

(51) Int. Cl.
*A61B 6/12* (2006.01)
*A61N 1/05* (2006.01)
*A61B 17/34* (2006.01)
*A61M 25/01* (2006.01)

(52) U.S. Cl.
CPC .............. *A61N 1/0587* (2013.01); *A61B 6/12* (2013.01); *A61B 17/3468* (2013.01); *A61M 25/0108* (2013.01); *A61N 1/057* (2013.01); *A61N 1/059* (2013.01); *A61N 2001/058* (2013.01)

(58) Field of Classification Search
CPC . A61B 17/3468; A61B 6/12; A61M 25/0108; A61N 1/057; A61N 1/0587; A61N 1/059; A61N 2001/058
See application file for complete search history.

(56) References Cited

U.S. PATENT DOCUMENTS

| | | |
|---|---|---|
| 8,010,209 B2 | 8/2011 | Jacobson |
| 8,504,156 B2 | 8/2013 | Bonner et al. |
| 2012/0172690 A1 | 7/2012 | Anderson et al. |
| 2012/0172891 A1 | 7/2012 | Lee |
| 2013/0079861 A1 | 3/2013 | Reinert et al. |
| 2013/0103047 A1 | 4/2013 | Steingisser et al. |
| 2013/0131591 A1 | 5/2013 | Berthiaume et al. |
| 2013/0131693 A1 | 5/2013 | Berthiaume et al. |

OTHER PUBLICATIONS

P0041402.WOU2 (PCT/US2015/023275) PCT Notification of Transmittal of the International Search Report and the Written Opinion of the International Searching Authority, Mailed Sep. 9, 2015, 11 pages.

*Primary Examiner* — Mark Remaly
(74) *Attorney, Agent, or Firm* — Evans M. Mburu

(57) ABSTRACT

A tool of an interventional medical systems system includes a core configured to be temporarily attached to the implantable medical device, as the tool deploys the device to expose a fixation member of the device for engagement with tissue at a target implant site; the core is then employed to verify adequate fixation of the deployed device via a tug test. An operator determines that the device is adequately fixed by the engaged fixation member, if a tug force that is applied to the core modifies the temporary attachment between the core and the device, to allow release of the device from the temporary attachment. A tether, which is fixedly attached to the core, may be employed to create the temporary attachment between the core and the device, or the temporary attachment may be created by a snap fit formed between the core and the attachment structure of the device.

8 Claims, 7 Drawing Sheets

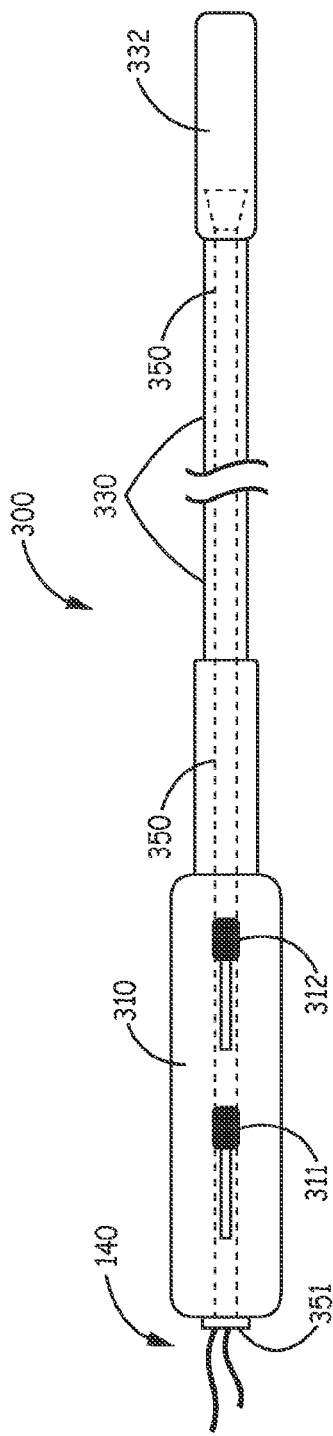
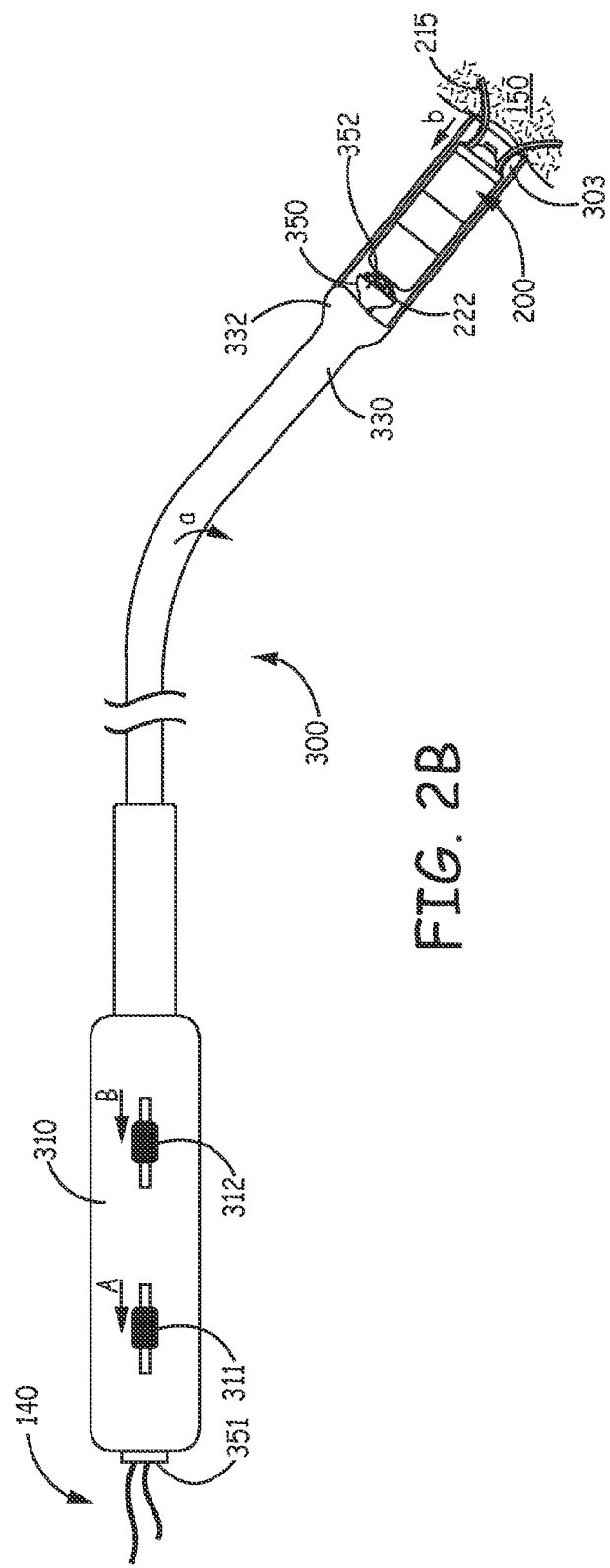

INTERVENTIONAL MEDICAL SYSTEMS, TOOLS, AND ASSOCIATED METHODS

CROSS-REFERENCE TO RELATED APPLICATION

The present application is related to the co-pending and commonly assigned U.S. patent application Ser. No. 14/231/976, filed on Apr. 1, 2014, entitled INTERVENTIONAL MEDICAL SYSTEMS, TOOLS, AND SUBASSEMBLIES, and which is incorporated by reference in its entirety.

FIELD OF THE DISCLOSURE

The present invention pertains to interventional medical systems, and more particularly to tools and related methods to facilitate percutaneous transvenous deployment and fixation verification of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode that is positioned at a pacing site, either endocardial or epicardial. Mechanical complications and/or MRI compatibility issues, which are sometimes associated with elongate lead wires, have motivated the development of implantable cardiac pacing devices that are wholly contained within a relatively compact package for implant in close proximity to the pacing site, for example, within the right ventricle RV of the heart. With reference to FIGS. 1A-B, such a device 200 is illustrated, wherein an hermetically sealed housing 205, preferably formed from a biocompatible and biostable metal such as titanium, contains a pulse generator, or an electronic controller (not shown), to which at least one electrode 211 is coupled, for example, by a hermetic feedthrough assembly (not shown) known to those skilled in the art of implantable medical devices. Housing 205 may be overlaid with an insulative layer, for example, medical grade polyurethane, parylene, or silicone.

FIG. 1A illustrates device 200 implanted at a target site 150 in the apex of the right ventricle RV, for example, being fixed in place by a fixation member 215 that includes a plurality of tines, which are better seen in FIG. 1B. Embodiments of the illustrated fixation member 215 are described in commonly assigned United States Patent application 2012/0172690, which is hereby incorporated by reference in its entirety. FIG. 1A further illustrates device 200 having been deployed out from a distal portion of an elongate delivery tool 100, for example, a guiding catheter, which has been maneuvered up through the inferior vena cava IVC and into the right ventricle RV from the right atrium RA, according to methods known in the art of interventional cardiology.

FIGS. 2A-B are plan views of a specialized tool 300 developed for the deployment of relatively compact implantable medical devices like device 200, in lieu of more common catheter-type tools, like tool 100. FIGS. 2A-B illustrate tool 300 including a handle assembly 310, an outer tube 330, and a core 350, for example, an inner elongate tube (shown with dashed lines in FIG. 2A), extending within outer tube 330. FIGS. 2A-B further illustrate outer tube 330 including a distal-most portion 332, which is sized to contain an implantable medical device, for example, the above-described device 200, which can be seen in the cut-away section of FIG. 2B, when a proximal end of the device, for example, attachment structure 222, abuts a distal member 352 of core/tube 350. Distal-most portion 332 also defines a distal opening 303 of outer tube 330, through which device 200 is deployed, for example, as shown in FIG. 2B, when outer tube 330 is withdrawn, or retracted, relative to core/tube 350, per arrow b, for example, by moving a control member 312 of handle assembly 310 per arrow B. With further reference to FIGS. 2A-B, handle assembly 310 includes another control member 311 to which a proximal end of a pull wire (not shown) may be attached; a distal end of the pull wire may be anchored adjacent to distal member 352 of core/tube 350, so that when control member 311 is moved per arrow A tool 300 is deflected per arrow a, as shown in FIG. 2B. The deflection, per arrow a, may be useful to position distal-most portion 332 in close proximity to target site 150 so that, upon retraction of outer tube 330, per arrow b, the aforementioned tines of fixation member 215 may engage with the tissue at site 150. Disclosure included in commonly assigned United States Patent Application 2013/0103047, which describes a general construction of a tool like tool 300, is hereby incorporated by reference.

With reference back to FIG. 1A, a tether 140 is shown extending from an attachment structure 222 of device 200 and back into tool 100, so that a proximal portion of tether 140, which extends out from a proximal end of tool 100, is accessible to an operator. With reference to FIG. 1B, attachment structure 222 includes an aperture 202 through which tether 140 may be looped to temporarily secure device 200 to tether 140. Tether 140 may similarly be secured to device 200, when device 200 is loaded in tool 300 for deployment. With reference to FIGS. 2A-B, the looped tether 140 extends within core/tube 350 so that ends of tether 140 extend from a proximal opening 351 of core 350, where the operator may tug on tether 140 to test the fixation of device 200 at the implant site, and, if necessary, apply a greater force to tether 140 to remove device 200 from the implant site for repositioning at a more suitable site. If the operator is satisfied with the performance of device 200 at the illustrated implant site, the operator may release tether 140 from attachment structure 122 and withdraw tether 140 through delivery tool 300.

SUMMARY

Because an operator performing a simple tug test, for example, as described above, does not necessarily know how much force to apply to verify adequate fixation of an implanted device, and because, from operator to operator, the applied tug force will not necessarily be the same, there is a need for the embodiments of interventional medical systems disclosed herein, which are configured to provide a calibrated tug test verification of adequate fixation for an implantable medical device at a target implant site. According to some embodiments, a tool of the system includes a core, which is configured to be temporarily attached to the implantable medical device, while the tool deploys the device by positioning and then exposing a fixation member of the device for engagement with tissue at a target implant site; the core is then employed to verify adequate fixation of the deployed device via a tug test. According to disclosed methods, the tug test is performed by applying a tug force to the core, and then, if the temporary attachment between the core and the device is modified by the tug force, to allow release of the device from the temporary attachment, the operator determines that the device is adequately fixed by the engaged fixation member. According to some methods, a tether, which has an end fixedly attached to the core of the tool, is employed to create the temporary attachment between the core and the device by threading a free end of the tether through an aperture of an attachment structure of the device and positioning a test segment of the tether just proximal to a channel within the core. The channel may be located in proximity to a distal opening of the core, and is configured to only allow distal passage of the test segment therethrough when the tug force is greater than or equal to a predetermined force that corresponds to an adequate device fixation force. According to some alternate methods, the temporary attachment between the core of the tool and the device is created by forming a snap fit between the core and the attachment structure of the device, wherein the tug force disengages the snap fit only when the tug force is greater than or equal to the predetermined force that corresponds to an adequate device fixation force. According to some embodiments, the core of the tool includes a distal opening and a distal member in which the distal opening is formed, wherein the distal member may include one or more inward protruding tabs positioned around the distal opening to form the snap fit around the attachment structure of the device, when the attachment structure is inserted through the distal opening.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 2A is a plan view of an exemplary delivery tool;

FIG. 2B is a plan view of an exemplary interventional medical system including the tool of FIG. 2A and the device of FIG. 1B;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1A:
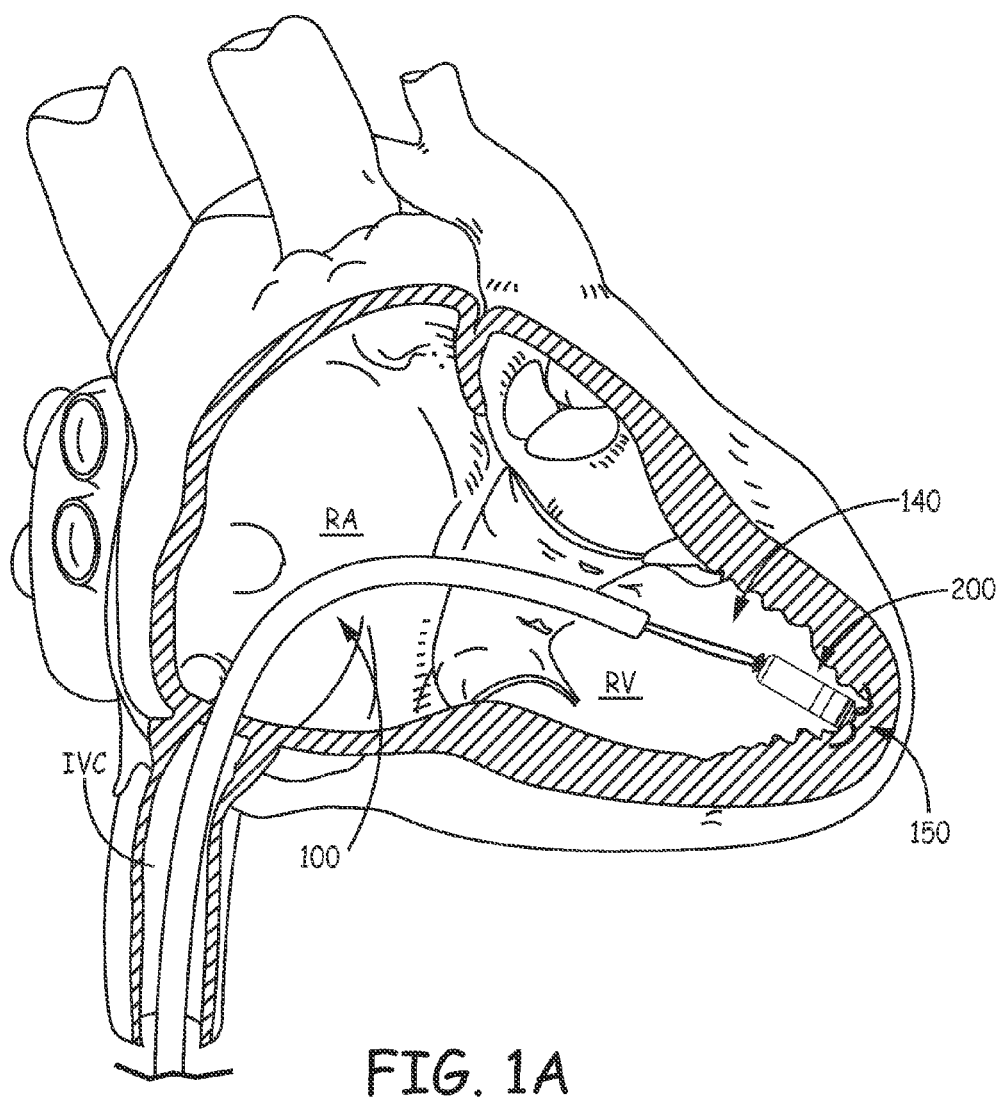
FIG. 1A is a schematic showing an implanted exemplary implantable medical device.
Figure 1B:
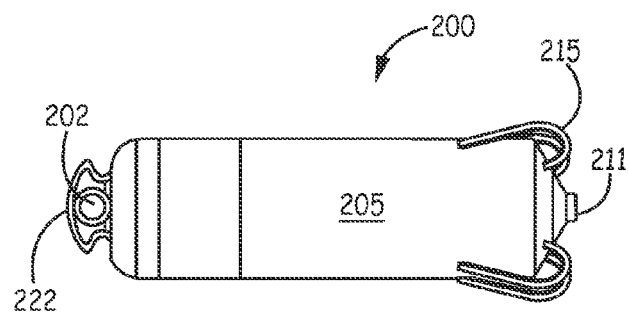
FIG. 1B is a plan view of the exemplary medical device.
Figure 3A:
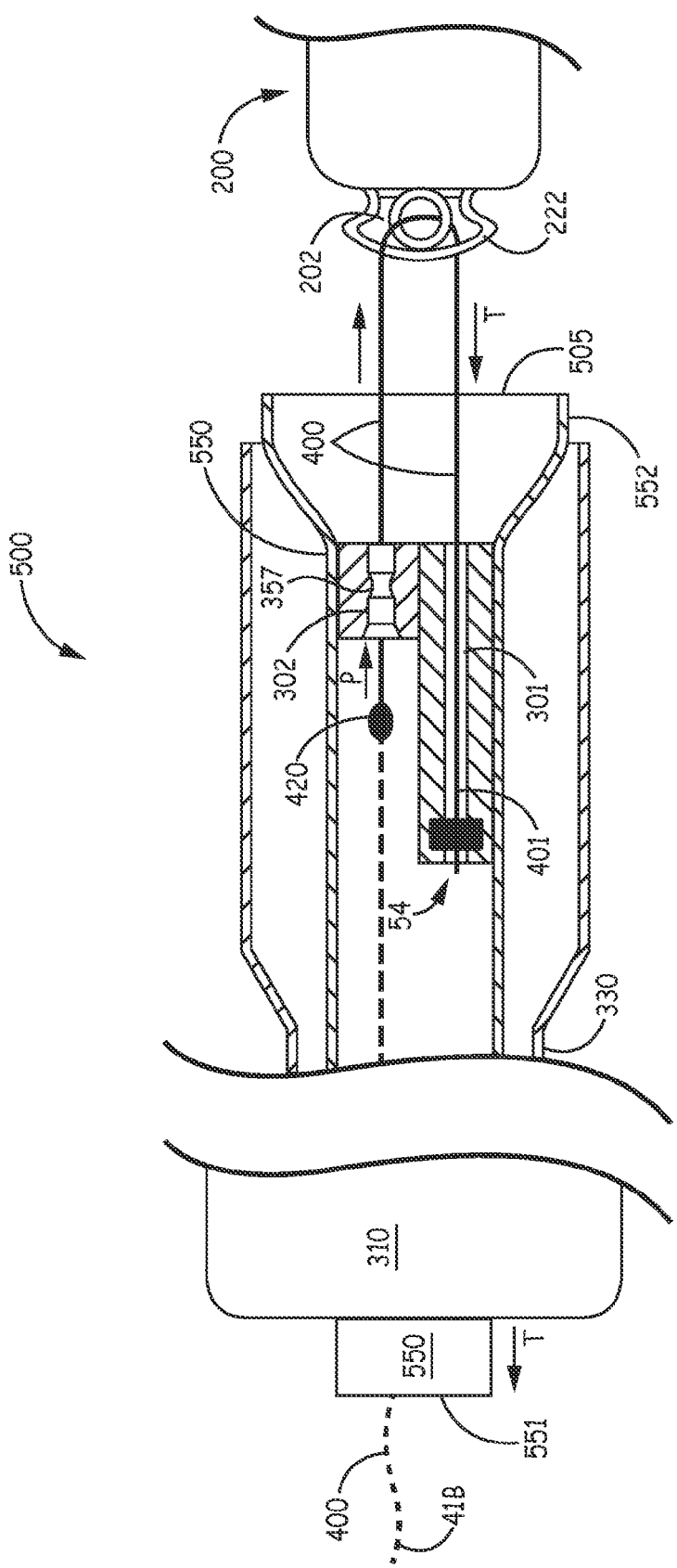
FIG. 3A is a plan view, which includes a cross-section view, of portions of an interventional medical system, according to some embodiments of the present invention.

FIG. 3A is a plan view of portions of an interventional system, like that shown in FIG. 2B, with a cross-section view through a distal end of a delivery tool 500. Delivery tool 500 differs from the above described tool 300, in that a core 550 thereof, which extends within outer tube 330 (in lieu of core 350), includes a channel 357 and a joint 54, for example, formed by an adhesive bond and/or by an interlocking fit, which fixedly attaches an end 401 of a tether 400 to core 550. FIG. 3A illustrates channel 357 located in proximity to a distal opening 505 of core 550, which may be defined by a distal member 552 of core 550. FIG. 3A further illustrates tether 400 having a length that extends from the fixed end 401, out through distal opening 505 of core 550, through aperture 202 of device attachment structure 222, and back into core 550, through distal opening 505, to test segment 420, which is located just proximal to channel 357. According to the illustrated embodiment, a radial cross-section of tether test segment 420 is enlarged, relative to a remainder of the length of tether 400, and is larger than the radial cross-section of channel, so that an interference fit between test segment 420 and channel 357, for example, approximately 0.001 interference, serves to temporarily attach device 200, via attachment structure 222 and tether 400, to core 550 of delivery tool 500. The temporary attachment can only be severed when a force, which corresponds to a predetermined adequate device fixation force, pulls test segment 420 through channel 357, per arrow P, for example, during a tug test that is described below in greater detail.

Figure 3B:
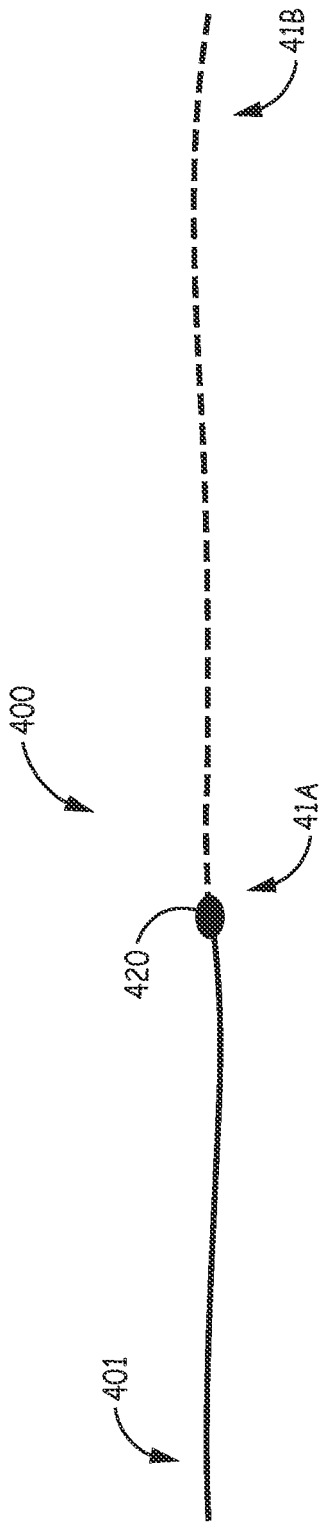
FIG. 3B is a plan view of some alternate embodiments of a tether portion of the system of FIG. 3A.
Figure 3C:
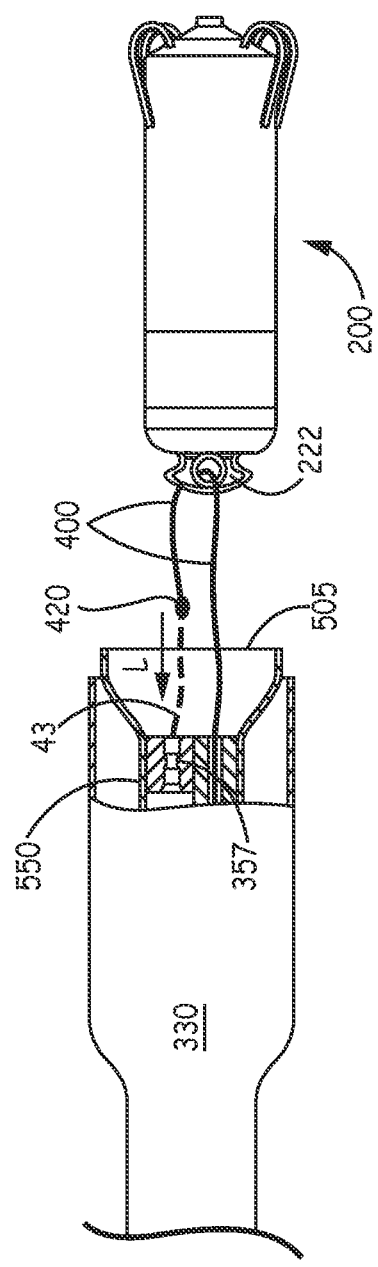
FIGS. 3C-D are additional plan views of the system of FIG. 3A, according to some embodiments.

FIG. 3B is a plan view of some alternate embodiments of tether 400, separate from core 550. In some embodiments, test segment 420 is located along the length of tether 400 and adjacent to a free end 41A of tether 400; while in other embodiments, the length of tether 400 is significantly longer (shown extended with a dashed line) so that a free end 41B thereof is spaced further apart from test segment 420 to be located outside a proximal opening 551 of core 550, when test segment 420 is positioned just proximal to channel 357, according to the dashed lines of FIG. 3A. With reference to FIG. 3C, the temporary attachment between device 200 and core 550 may be formed by threading free end 41A/41B of tether 400 through device attachment structure 222, and then positioning tether test segment 420 within core 550, either by pulling on tether free end 41A/41B to draw test segment 420 through channel 357, per arrow L, for example, with an elongate stylet (not shown) that can extend within core 550, from proximal opening 551 to tether free end 41A/41B, or by pushing test segment 420, per arrow L, through channel 357, via distal opening 505, for example, with a plunger type tool (not shown).

According to an exemplary embodiment, the length of tether 400 is formed from any suitable biocompatible fiber, for example, a polyester fiber that has a fluoropolymer coating, such as PTFE, and test segment 420 may be formed a biocompatible polymer material such as a polyether block amide, for example, PEBAX® 3533 or 4033, silicone, or polyurethane. According to some exemplary embodiments, test segment 420 is positioned around an elongate fiber of tether 400 and is fixedly coupled thereto at a location along the length of tether 400, either adjacent to tether free end 41A, or spaced apart from tether free end 41B, as described above. For example, test segment 420 may be insert-molded around the fiber, or test segment 420 may be formed with a throughhole, through which the fiber of tether 400 is threaded and subsequently bonded therein, for example, with any suitable biocompatible adhesive known in the art. The material forming test segment 420, for example, polyurethane or one of the aforementioned PEBAX® materials, may be blended with another material, for example, 10% Siloxane, to make an external surface of test segment 420 more lubricious.

With further reference to FIG. 3A, first and second lumens 301, 302 of tube 505, including channel 357, may be formed by an insert member, for example, which is formed from a biocompatible polymer material, such as PEBAX® 3533 or 4033, silicone, or polyurethane, and which is fixedly attached to a wall of tube 550, wherein a remainder of tube 550 may be formed from a similar material. The insert member may be molded separately and then bonded to the wall of tube 550 (e.g., via thermal bonding or adhesive bonding according to methods known in the art). Alternately, the insert member may be insert-molded together with the wall of tube 550. According to some embodiments, a surface of lumen 301 is fixedly adhered to end 401 of tether 400 to form the aforementioned joint 54, for example, by adhesive bonding and/or insert-molding. Alternately, or in addition, joint 54 includes a mechanical interlock between tether end 401 and first lumen 301 of insert member 67, for example, as illustrated in FIG. 3A.

With reference back to FIG. 2B, the operator may manipulate tool 500, like tool 300, as described above, to deploy device 200 through distal opening 303 of outer tube 330, so that tines of fixation member 215 engage with the tissue at site 150, while device 200 is temporarily attached to core 550 via tether 400, as described above. With further reference to FIG. 3A, once device 200 is fixed at site 150, the operator can evaluate the fixation of the engaged tines by performing a tug test by applying a tug force, per arrow T, to core 550, for example, by grasping and pulling on handle assembly 310, to which core 550 is fixedly attached, or by grasping and pulling directly on a proximal portion of core 550 in proximity to handle assembly 310. Test segment 420 is pulled through channel 357, per arrow P, only by a tug force, per arrow T, that is greater than or equal to a predetermined force, wherein the predetermined force corresponds to a minimum adequate fixation force for device 200, for example, provided by engaged fixation member 215. Thus, if device 200 is not adequately fixed at site 150, the applied tug force will dislodge the engagement of the tines without pulling test segment 420 through channel 357, but, if the tug force pulls test segment 420 of tether 400 through channel 357, per arrow P, the operator can be assured that device 200 is adequately fixed at site 150. An adequate fixation force for device 200 may be approximately 1.5 Newtons.

According to some embodiments, test segment 420 is radiopaque, for example, being formed from either the aforementioned PEBAX® materials blended with a radiopaque material, for example, 40% Barium Sulfate (BaSO4), Bismuth Subcarbonate, or tungsten, so that the operator may monitor the position of test segment 420. If test segment 420 of tether 400 is radiopaque, and if channel 357 of the insert member is also formed from a radiopaque material (e.g., similar to that of test segment 420), the operator may monitor, via fluoroscopy, a position of test segment 420 relative to channel 357 during the above described tug test. Alternately, if channel 357 is not radiopaque, distal member 552 of core 550 may be radiopaque, so that the operator may monitor, via fluoroscopy, the position of a radiopaque test segment 420 relative to distal member 552. Thus, when the operator sees, via fluoroscopy, radiopaque test segment 420 merging with the radiopaque distal member 552 during the tug test, the operator may be assured that the tug force has pulled test segment 420 through channel 357, which is located proximal to distal member 552. According to an exemplary embodiment, distal member 552 is formed from a radiopaque material, such as PEBAX® 7033 blended with BaSO4, separate from a remainder of tube 550 before being bonded thereto.

Figure 3D:
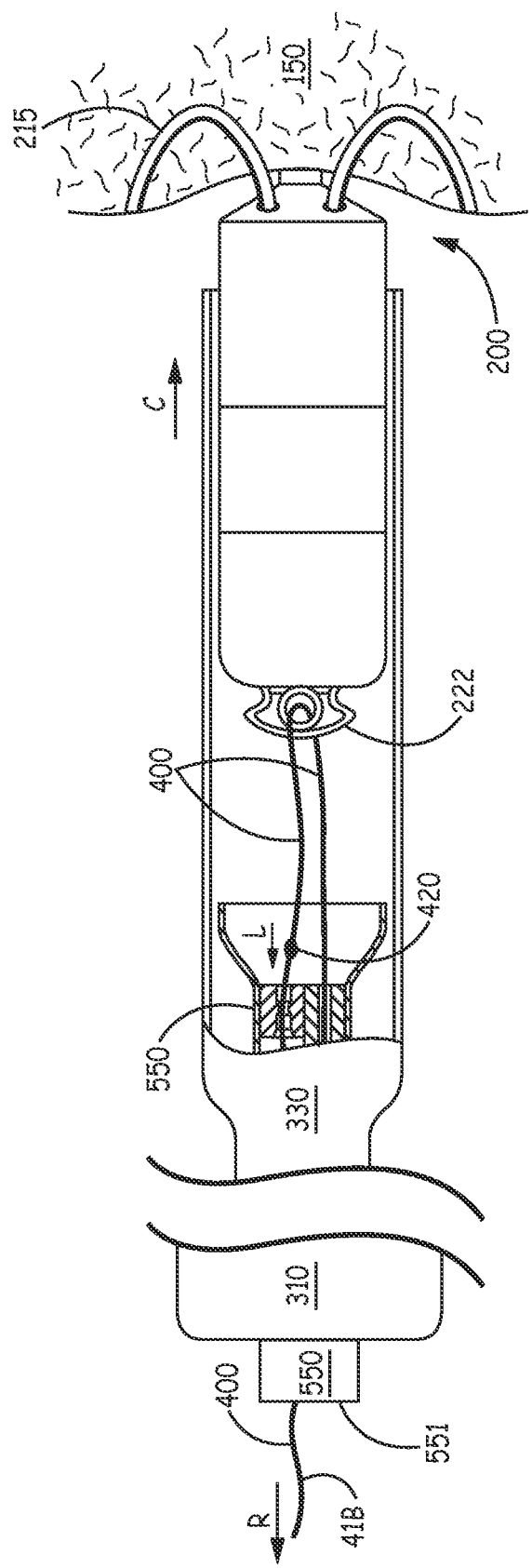

FIG. 3A further illustrates free end 41B of tether 400 located in proximity to proximal opening 551 of core 550, and tether 400 having a sufficient length so that free end 41B may be employed to re-create the temporary attachment between device 200 and core 550, for example, as shown in FIG. 3D. FIG. 3D illustrates a force, per arrow R, which may be applied to tether free end 41B to pull tether test segment 420 back through channel 357 of inner tube 550, per arrow L, thereby re-creating the temporary attachment between device 200 and core 550 of delivery tool 500. Then, device 200 may be extracted from implant site 150 for repositioning at another implant site, for example, by pulling on core 550 and tether free end 41B, with a force sufficient to disengage the tines of device fixation member 215, and advancing outer tube 330 of the tool, per arrow C, back over device 200, for example by moving control member 312 of handle assembly 310 in an opposite direction to that designated by arrow B in FIG. 2B.

Figure 4A:
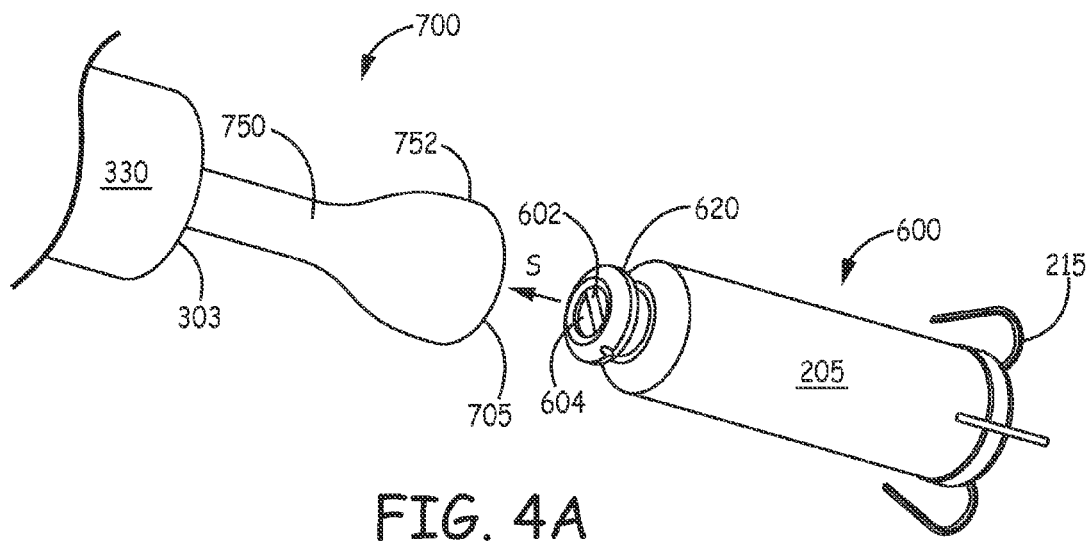
FIG. 4A is a perspective view of portions of an interventional medical system, according to some alternate embodiments.
Figure 4B:
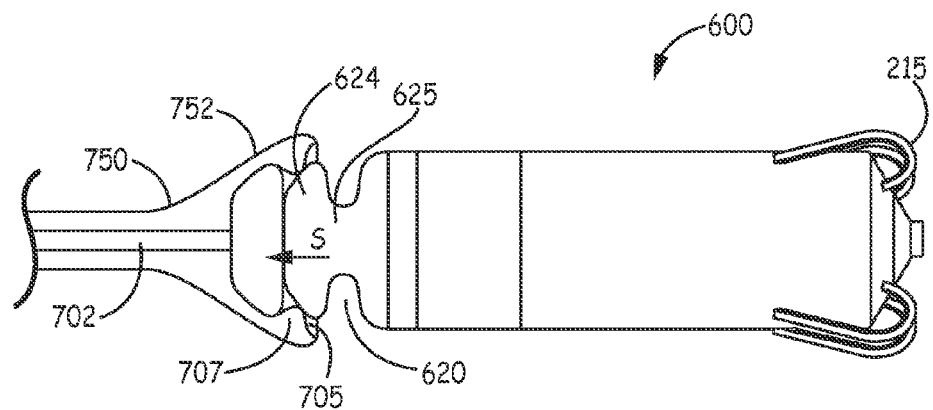
FIGS. 4B-C are plan views, which each include a partial cross-section view, of the system of FIG. 4A, according to some embodiments.
Figure 4C:
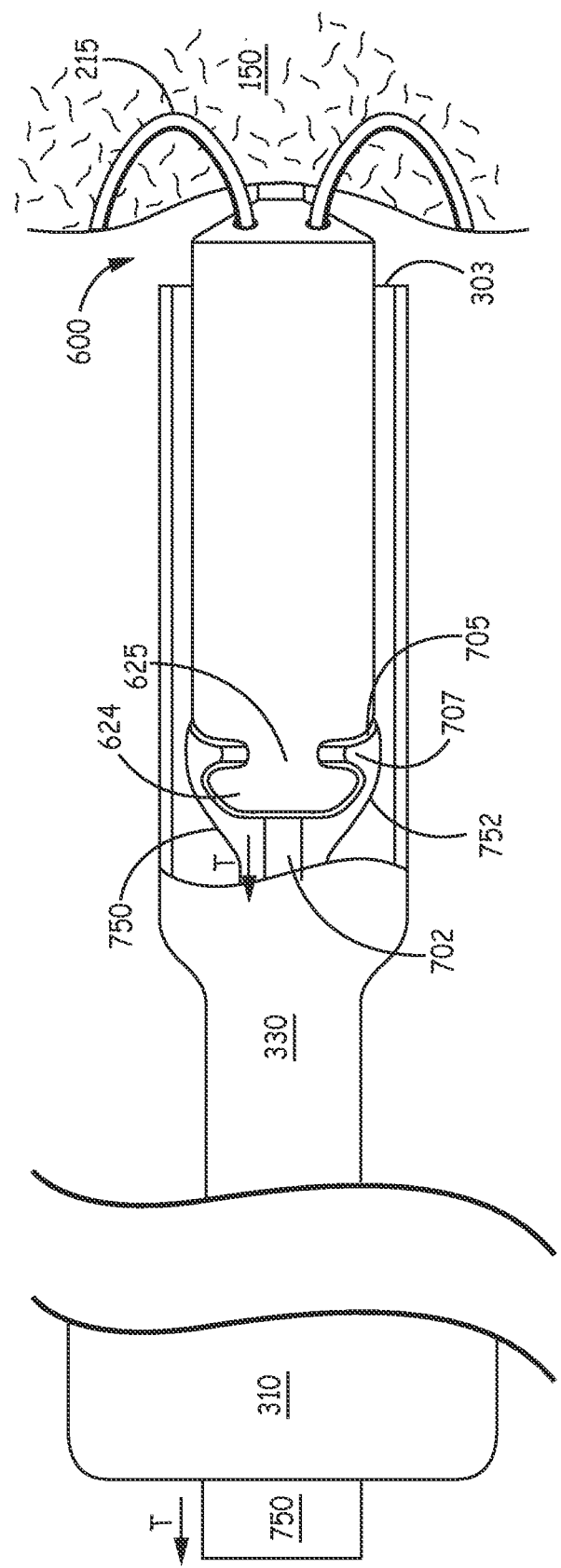

FIG. 4A is a perspective view of portions of an interventional medical system, according to some alternate embodiments. FIG. 4A illustrates the system including an implantable medical device 600 and a delivery tool 700, wherein device 600 is positioned for creating a temporary attachment between an attachment structure 620 thereof and a core 750 of tool 700. FIG. 4A further illustrates core 750 including a distal member 752 in which a distal opening 705 of core 750 is formed, and toward which attachment structure 620 of device 600 is directed, per arrow S, for a snap fit that creates the temporary attachment. FIG. 4B is a plan view, which includes a cross-section view through core 750 that shows one or more inward protruding tabs 707 of distal member 752 positioned around distal opening 705. According to the illustrated embodiment, a deformation of distal member 752 and/or tab(s) 707 allows the insertion of a head 624 of attachment structure 620 through distal opening 705 and into distal member 752 of core 750, per arrow S. Then, with reference to FIG. 4C, tab(s) 707 interlock around a necked-down segment 625 of the fully inserted attachment structure 620 to form the snap fit. FIGS. 4B-C further illustrate core 750 including an optional lumen 702, for example, to accommodate a tether (not shown), which is temporarily secured to attachment structure 620, for example, around a bar 602 that spans a cavity 604 thereof. It should be noted that, according to some alternate embodiments, distal member 752 of core 750 may be configured to form a snap fit within cavity 604 of attachment structure 620, such that distal opening 705 need not be included.

Delivery tool 700, like the above-described tools 300, 500, includes outer tube 330 in which core 750 extends, and may be manipulated in a similar fashion to deploy device 600 through distal opening 303 of outer tube 330, so that tines of fixation member 215 engage with the tissue at site 150, while attachment structure 620 of device 600 is temporarily attached to core 750 by the snap fit, for example, as shown in FIG. 4C. The snap fit disengages to release device 600 only when a tug force, per arrow T, is greater than or equal to the above described predetermined force, which corresponds to an adequate fixation force for device 600, for example, provided by engaged tines of fixation member 215 at implant site 150. Thus, if device 600 is not adequately fixed at site 150, the applied tug force will dislodge the engagement of the tines without disengaging the snap fit, but, if the tug force disengages the snap fit, the operator can be assured that device 600 is adequately fixed at site 150. The tug force may be applied to core 750, by grasping and pulling on handle assembly 310, to which core 750 is fixedly attached, or by grasping and pulling directly on core 750 in proximity to handle assembly 310.

Distal member 752 may be formed separately from a remainder of core 750, for example, from any suitable biocompatible elastic material, such as polyether block amide, polyurethane, or nylon, wherein one more tabs 707 are integrally formed, and then bonded or otherwise joined thereto. Distal member 752 may be radiopaque, for example, being formed from PEBAX® 7233 blended with 40% BaSO4. According to an exemplary embodiment, distal member 752 is molded with an inward protruding ridge that extends 360 degrees around distal opening 705 to form the one or more tabs 707, wherein a diameter of distal opening 705 may taper inward from between approximately 5 mm to 7 mm to approximately 3 mm to 4.5 mm where the ridge is formed.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical system comprising an implantable device and a delivery tool facilitating deployment of the implantable device, the device including an attachment structure and a fixation member, the fixation member being configured to engage tissue at an implant site and thereby fix the device at the implant site; and the tool comprising an outer tube and a core, the outer tube comprising a distal-most portion sized to receive the device therein, the core extending within the outer tube, and the core comprising:

a distal member located within the distal-most portion of the outer tube, the distal member being configured to form a snap fit with the attachment structure of the device, the snap fit temporarily attaching the device to the tool; and wherein the snap fit of the distal member disengages to release the attached device, only when a tug force, applied to the core of the tool, is greater than or equal to a predetermined force, the predetermined force corresponding to a minimum adequate fixation force of the engaged fixation member fixing the device at the implant site.

2. The system of claim 1, wherein:

the core of the tool further comprises a distal opening formed in the distal member thereof; and the distal member of the core comprises one or more inward protruding tabs positioned around the distal opening and configured to interlock around the device attachment structure to form the snap fit.

3. The system of claim 2, wherein the one or more inward protruding tabs of the distal member of the core comprise an inward protruding ridge that extends 360 degrees around the distal opening of the core.

4. The system of claim 1, wherein the distal member of the core of the tool is radiopaque.

5. A delivery tool facilitating deployment of an implantable medical device, the device including an attachment structure and a fixation member, the fixation member being configured to engage tissue at an implant site and thereby fix the device at the implant site, and the tool comprising:

an elongate core including a distal member configured to form a snap fit with the attachment structure of the device, the snap fit temporarily attaching the device to the tool; and wherein the snap fit of the distal member disengages to release the attached device, only when a tug force, applied to the core, is greater than or equal to a predetermined force, the predetermined force corresponding to a minimum adequate fixation force of the engaged fixation member fixing the device at the implant site.

6. The tool of claim 5, wherein:

the elongate core further includes a distal opening formed in the distal member; and the distal member of the core comprises one or more inward protruding tabs positioned around the distal opening and configured to interlock around the device attachment structure to form the snap fit.

7. The tool of claim 6, wherein the one or more inward protruding tabs of the distal member of the core comprise an inward protruding ridge extending 360 degrees around the distal opening of the core.

8. The tool of claim 5, wherein the distal member of the core is radiopaque.

* * * * *